(12) United States Patent
McGinnis et al.

(10) Patent No.: US 7,202,341 B2
(45) Date of Patent: Apr. 10, 2007

(54) STABILIZED HEMOGLOBIN SOLUTIONS

(75) Inventors: Robert McGinnis, Park Ridge, IL (US); Gabriel Chavez, Chicago, IL (US); Marc Doubleday, Cary, IL (US); Richard DeWoskin, St. Charles, IL (US); Anthony Avella, Crystal Lake, IL (US)

(73) Assignee: Northfield Laboratories, Inc., Evanston, IL (US)

( * ) Notice: Subject to any disclaimer, the term of this patent is extended or adjusted under 35 U.S.C. 154(b) by 0 days.

(21) Appl. No.: 11/231,921

(22) Filed: Sep. 21, 2005

(65) Prior Publication Data
US 2006/0014671 A1    Jan. 19, 2006

Related U.S. Application Data

(63) Continuation of application No. 10/124,941, filed on Apr. 18, 2002, now abandoned.

(51) Int. Cl.
C07K 14/805 (2006.01)
A61K 38/16 (2006.01)
A61B 19/02 (2006.01)

(52) U.S. Cl. .................. 530/385; 514/6; 604/403; 604/408

(58) Field of Classification Search ................ 530/385; 514/6; 604/403, 408
See application file for complete search history.

(56) References Cited

U.S. PATENT DOCUMENTS

| | | | |
|---|---|---|---|
| 4,001,200 A | 1/1977 | Bonsen et al. | |
| 4,001,401 A | 1/1977 | Bonsen et al. | |
| 4,053,590 A | 10/1977 | Bonsen et al. | |
| 4,061,736 A | 12/1977 | Bonsen et al. | |
| 4,140,162 A | 2/1979 | Gajewski et al. | |
| 4,460,365 A | 7/1984 | Ganshirt et al. | |
| 4,538,981 A | 9/1985 | Venturini | |
| 4,561,110 A | 12/1985 | Herbert | |
| 4,670,417 A | 6/1987 | Iwasaki et al. | |
| 4,699,816 A | 10/1987 | Galli | |
| 4,704,402 A | 11/1987 | Abraham et al. | |
| 4,826,811 A | 5/1989 | Sehgal et al. | |
| 4,826,955 A | 5/1989 | Akkapeddi et al. | |
| 4,857,636 A | 8/1989 | Hsia | |
| 4,861,867 A | 8/1989 | Estep | |
| 4,988,515 A | 1/1991 | Buckberg | |
| 5,045,529 A | 9/1991 | Chiang | |
| 5,051,353 A | 9/1991 | Stratton et al. | |
| 5,084,558 A | 1/1992 | Rausch et al. | |
| 5,100,401 A | 3/1992 | Patel | |
| 5,167,657 A | 12/1992 | Patel | |
| 5,178,884 A | 1/1993 | Goodrich et al. | |
| 5,189,146 A | 2/1993 | Hsia | |
| 5,194,590 A | 3/1993 | Sehgal et al. | |
| 5,206,075 A | 4/1993 | Hodgson, Jr. | |
| 5,234,903 A | 8/1993 | Nho et al. | |
| 5,241,031 A | 8/1993 | Mehta | |
| 5,264,555 A | 11/1993 | Shorr et al. | |
| 5,272,236 A | 12/1993 | Lai et al. | |
| 5,278,272 A | 1/1994 | Lai et al. | |
| 5,296,465 A | 3/1994 | Rausch et al. | |
| 5,296,466 A | 3/1994 | Kilbourn et al. | |
| 5,334,706 A | 8/1994 | Przybelski | |
| 5,352,773 A | 10/1994 | Kandler et al. | |
| 5,356,709 A | 10/1994 | Woo et al. | |
| 5,438,041 A | 8/1995 | Zheng et al. | |
| 5,439,882 A | 8/1995 | Feola et al. | |
| 5,464,814 A | 11/1995 | Sehgal et al. | |
| 5,683,768 A | 11/1997 | Shang et al. | |
| 5,691,452 A * | 11/1997 | Gawryl et al. | ............... 530/385 |
| 5,691,453 A | 11/1997 | Wertz et al. | |
| 5,695,840 A | 12/1997 | Mueller | |
| 5,929,031 A | 7/1999 | Kerwin et al. | |
| 5,988,422 A | 11/1999 | Vallot | |
| 6,027,776 A | 2/2000 | Mueller | |
| 6,076,457 A | 6/2000 | Vallot | |
| 6,127,043 A | 10/2000 | Lange | |
| 6,133,425 A | 10/2000 | Sehgal et al. | |
| 6,271,351 B1 * | 8/2001 | Gawryl et al. | ............... 530/385 |

(Continued)

FOREIGN PATENT DOCUMENTS

GB    2107191    4/1983

(Continued)

OTHER PUBLICATIONS

"Film Preserves Blood Substitute," Pharmaceutical & Medical Packaging News, Jul. 1998.

(Continued)

*Primary Examiner*—Jon Weber
*Assistant Examiner*—Abdel A. Mohamed
(74) *Attorney, Agent, or Firm*—McDonnell Boehnen Hulbert & Berghoff LLP

(57) ABSTRACT

A hemoglobin solution packaged in a flexible oxygen-impermeable container system. The container system includes a multi-layer film having at least a product contact layer, an oxygen and moisture barrier layer and an exterior layer. The flexible container system further includes an interface port for filling the flexible container with the hemoglobin solution and delivering the hemoglobin solution. The hemoglobin solution comprises a substantially stroma and tetramer free, cross linked, pyridoxylated hemoglobin solution including preservatives such as ascorbic acid, glycine and dextrose.

27 Claims, 6 Drawing Sheets

U.S. PATENT DOCUMENTS 6,288,027 B1    9/2001    Gawryl et al.

FOREIGN PATENT DOCUMENTS

| WO | 8912456 | 12/1989 |
|----|---------|---------|
| WO | 9202239 | 2/1992 |
| WO | 9629346 | 9/1996 |
| WO | 9735883 | 10/1997 |
| WO | 9918979 | 4/1999 |
| WO | 0021366 | 4/2000 |
| WO | 0101775 | 1/2001 |
| WO | 0101921 | 1/2001 |

OTHER PUBLICATIONS

"Improved Barrier: Longer Life for Lifesaving Blood Product," Packaging World, p. 70, Sep. 1998.

DeVenuto, et al., Preparation and Evaluation of Pyridoxalated Polymerized Human Hemoglobin, Journal of Surgical Research, 34:205-212 (1983).

DeVenuto, et al., Characteristics of Stroma-free Hemoglobin Prepared by Crystallization, J. Lab. Clin. Med, 89:509-516 (1977).

Devenuto, F., Hemoglobin Solutions as Oxygen-Delivering Resuscitation Fluids, 10:238-245 (1982).

DeVenuto, F., Modified Hemoglobin Solution as a Resuscitation Fluid, Vox Sang, 44:129-142 (1983).

Sehgal, et al., Preparation and in vitro Characteristics of Polymerized Pyridoxylated Hemoglobin, Transfusion, 23:158-162 (1983).

Berger, et al., Achieving Efficacy and Sterility in Flexible Packaging, Medical Device & Diagnostic Industry, Aug. 2001.

Kothe, et al, Characterization of a Modified, Stroma-Free Hemoglobin Solution as an Oxygen-Carrying Plasma Substitute, Surgery, Gynecology & Obstetrics 161:563-569 (1985).

Sehgal, et al., Large-Volume Preparation of Pyridoxylated Hemoglobin with High $P_{50}^{1.2}$, Journal of Surgical Research, 30:14-19 (1981).

Savitsky, et al., A Clinical Safety Trial of Stroma-Free Hemoglobin, Clin. Pharmacol Ther., 73-80 (1978).

Issekutz, Andrew, Removal of Gram-Negative Enotoxin from Solutions by Affinity Chromatography, Journal of Immunological Methods, 61:275-281 (1983).

Mok, Winnie, Cross-linked Hemoglobins as Potential Plasma Protein Extenders, Federation Proceedings, 34:1458-1460 (1975).

* cited by examiner

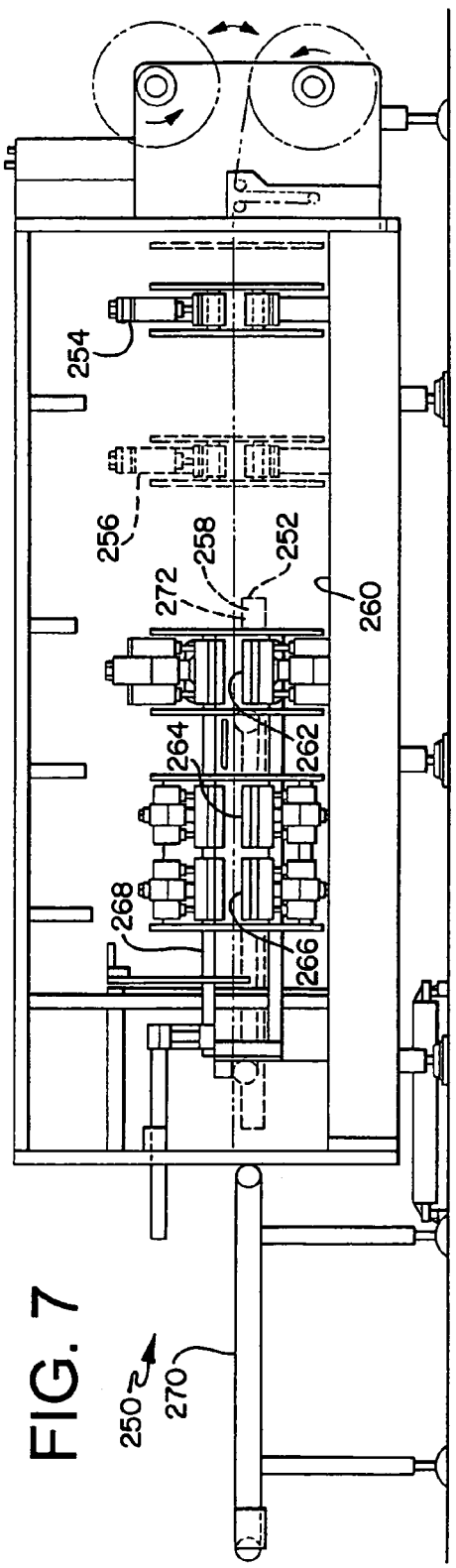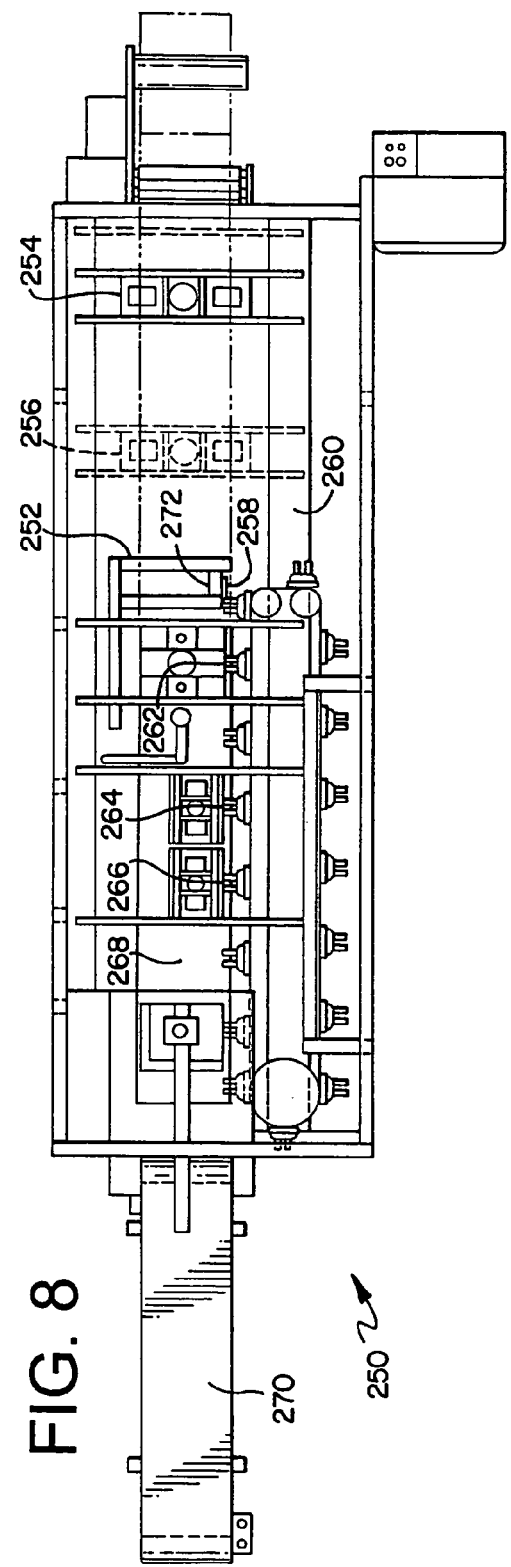

STABILIZED HEMOGLOBIN SOLUTIONS

This is a continuation of application Ser. No. 10/124,941 filed Apr. 18, 2002 now abandoned.

FIELD OF THE INVENTION

The invention relates to stabilized oxygen carrying solutions. More specifically, it relates to a hemoglobin solution packaged in an oxygen and water vapor impermeable flexible container, and to the storage and preservation of a deoxygenated hemoglobin solution.

BACKGROUND OF THE INVENTION

There is a consistent need for ready blood products for an ever-increasing surgical and trauma load, and to supplement blood bank shortages. Oxygen carrying solutions, such as hemoglobin-derived solutions can be used in place of whole blood or red blood cells for patients having a need for augmented oxygen carrying capacity. Because they are not dependent upon donor availability, such solutions can be made readily available in an emergency situation or during a blood bank shortage. Also, due to risk of infection of blood borne pathogens as a result of a blood transfusion, a patient may prefer a hemoglobin-derived solution for transfusion in place of whole blood or red blood cells. In particular, such solutions may include, but are not limited to, oxygen carriers, blood substitutes, and hemoglobin-derived compositions such as those disclosed in U.S. Pat. Nos. 6,133,425, 5,464,814, 5,438,041, 5,217,648, 5,194,590, 5,061,688, and 4,826,811, the teachings of which are incorporated herein by reference in their entirety.

Active hemoglobin is an oxygen ($O_2$) transporting protein found in red blood cells. Each hemoglobin molecule is comprised of four protein chains and four porphyrin molecules known as heme. In the middle of each heme is an iron atom that is partially oxidized to the (+2) state. When oxygen is transported under normal conditions in vivo, oxygen is bound to the heme without a change in valence of the iron ion; the hemoglobin thus becomes oxyhemoglobin. To indicate that this binding occurs without a change in valence, the reaction is called oxygenation (rather than oxidation), and the reverse process is deoxygenation. Hemoglobin is called deoxyhemoglobin to emphasize its oxygen free state.

Apart from oxygenation of the heme group, further oxidation of the iron atom can occur; the result is conversion of the bivalent iron ion to the trivalent state (+3). Hemoglobin having an oxidized heme group is known as methemoglobin. Human blood normally contains only a very small percentage of methemoglobin, but the amount can be increased by certain toxins and in some diseases. Such a condition is dangerous because methemoglobin does not transport $O_2$ to the body tissues.

Because methemoglobin does not transport $O_2$, the presence of methemoglobin in a hemoglobin solution should be avoided. Accordingly, the storage and handling of hemoglobin solutions is a critical part of their effectiveness. Storage requirements include the need to maintain the hemoglobin solutions in an essentially oxygen free environment in order to prevent the oxidation of hemoglobin to methemoglobin.

A common storage container for a medical solution, such as a hemoglobin solution, is a flexible container made of plastic polymer film, most notably an I.V. bag. Unlike I.V. bags for many other solutions, I.V. bags used specifically for hemoglobin solutions stored in a deoxygenated state must also provide a sufficient barrier to the passage of moisture vapor and other gasses to preserve the deoxygenated state of the hemoglobin solution contained therein. Further, the container for a hemoglobin solution should be made from a material that complies with U.S. Pharmacopeia (USP) Class VI classification (physical, chemical and biocompatibility) and that is non-pyrogenic.

In addition, these bags must meet a number of performance criteria, including collapsibility, optical clarity and transparency, and mechanical strength. Collapsibility is necessary in order to ensure proper and complete delivery or drainage of the bag. In order for the bag to be collapsible, the film from which the bag is made must be flexible. Thus, a key consideration in the design of films used to produce medical solution bags is that the film must have sufficient flexibility that the resultant medical bag is collapsible enough to be fully drainable. The container must be optically clear so that, prior to administering a medical solution from a bag and into a patient, a visual inspection of the solution contained within the container may be performed to determine whether the solution has deteriorated or has been contaminated. Therefore, it is essential that the container meet a level of optical properties, i.e., a high degree of clarity and transmission of light.

Typically, hemoglobin solutions cannot be terminally heat sterilized due to the degradation of the hemoglobin molecule and therefore must be aseptically filled. Thus, for purposes of sterilization, the containers must be, for example, gamma irradiated or washed in a hydrogen peroxide bath or exposed to an ethylene oxide environment. Therefore, another requirement of medical solution containers is that they must be able to endure the high dosages of gamma irradiation without discoloration or deterioration due to material degradation via polymer chain scissioning.

Finally, medical solution containers must also have sufficient mechanical strength to withstand the abuse which is typically encountered in the administration and handling of the solution. For example, in some circumstances, a plastic or rubber bladder is placed around a medical solution-containing bag and pressurized to, for example, approximately 300 mm Hg, in order to force the solution out of the pouch and into a patient. Such a bladder is commonly referred to as a "pressure-cuff" and is used, for example, when a patient is bleeding profusely in order to quickly replace lost fluids and restore oxygen carrying capacity or, for example, when resistance in the intravenous fluid path is high (e.g., long lines, small catheter, etc.) such that a greater opposing pressure must be generated in the bag in order to introduce in a timely fashion the medical solution into the patient.

SUMMARY OF THE INVENTION

The invention provides a packaged hemoglobin solution which is a substantially oxygen-free, polymerized hemoglobin solution sealed within a flexible container comprising a polymer film having an oxygen permeability of about 0.05 to about 0.3 cc/m² per 24 hours per atmosphere at about 5° C. and an external relative humidity of about 60%. Preferably, the hemoglobin solution is packaged in a polymer film having an oxygen permeability of either (a) about 0.05 to about 0.17 cc/m² per 24 hours per atmosphere at about 5° C. and an external relative humidity of about 60%, or (b) about 0.15 to about 0.5 cc/m² per 24 hours per atmosphere at about 25° C. and an external relative humidity of about 60%.

In certain embodiments of the invention, the methemoglobin concentration of the solution is less than about 8.0% for at least one year at about 5° C. and an external relative humidity of about 60%. In other embodiments, the solution may include an essentially tetramer-free, substantially stroma-free, cross-linked, polymerized, pyridoxylated hemoglobin.

In still another embodiment the hemoglobin solution contains one or more preservatives such as ascorbic acid or glycine.

In yet another embodiment, the invention provides a hemoglobin solution packaged in a polymer film which has an oxygen barrier layer. The oxygen barrier layer may include ethylene vinyl alcohol or PVDC.

Still another embodiment of the invention includes a hemoglobin solution which is a substantially oxygen-free, polymerized, pyridoxylated hemoglobin solution sealed within a flexible polymeric container comprising an oxygen barrier film having at least one barrier layer for maintaining the methemoglobin concentration of the solution below about 8.0% for at least one year at about 5° C.

The invention further provides for a method of preparing a deoxygenated hemoglobin solution that includes sealing a polymerized hemoglobin solution within a flexible container of a polymer film having an oxygen permeability of about 0.15 to about 0.5 cc/m$^2$ per 24 hours per atmosphere at about 25° C. and an external relative humidity of about 60%. The hemoglobin solution contains at least one oxygen scavenger capable of reducing $O_2$.

BRIEF DESCRIPTION OF THE DRAWINGS

Specific embodiments of the invention are described with reference to the following drawings, wherein:

FIG. 7 is a side view of the assembly process for manufacturing the flexible container system in accordance with a preferred embodiment of the present invention; and FIG. 8 is a top view of the assembly process for manufacturing the flexible container system in accordance with a preferred embodiment of the present invention.

DETAILED DESCRIPTION

Figure 1A:
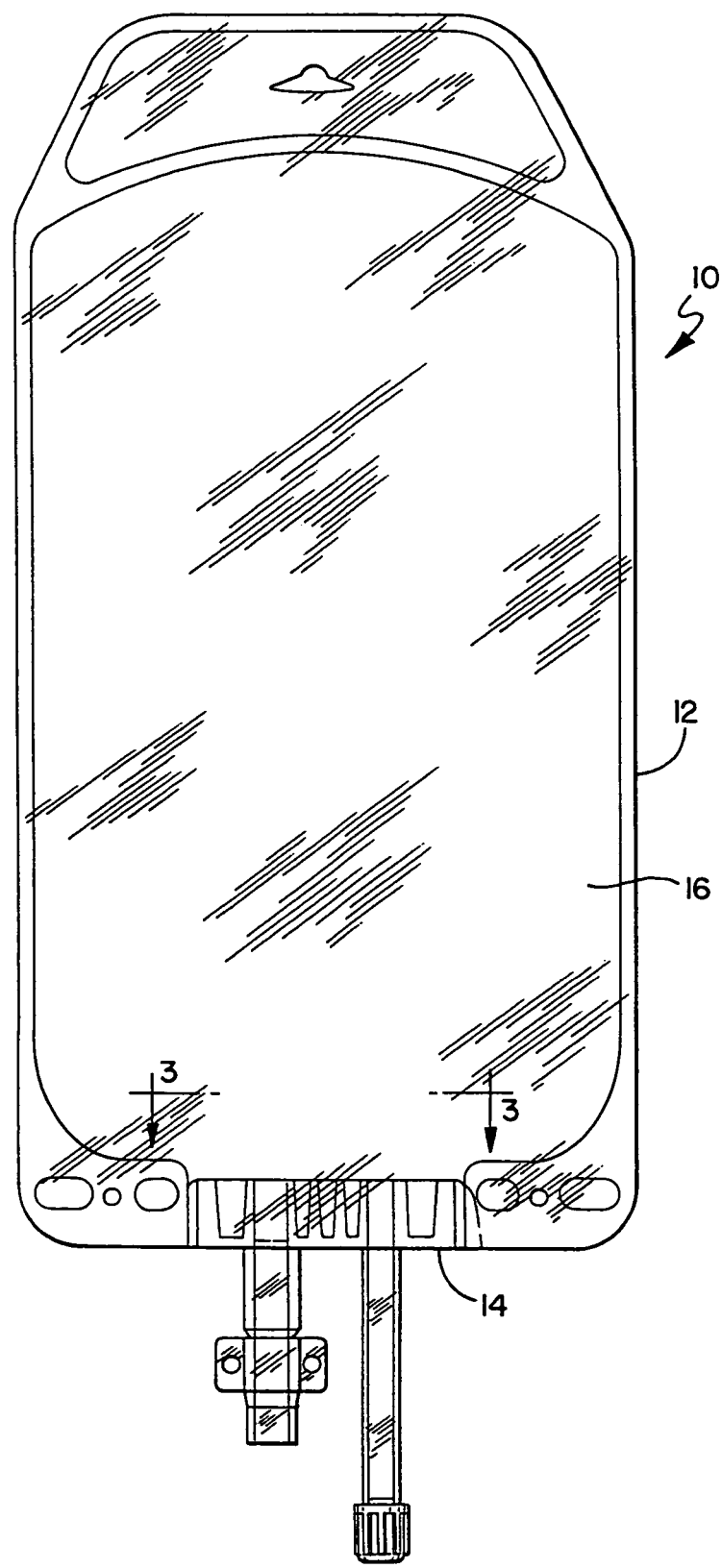
FIGS. 1A and 1B are plan views illustrating preferred embodiments of the flexible container system for an aqueous material in accordance with the present invention.

The present invention provides a stabilized deoxygenated hemoglobin solution packaged in an oxygen impermeable container. Preferably, the hemoglobin solution is an acellular red blood cell substitute comprising an essentially tetramer-free, cross-linked, polymerized, pyridoxylated hemoglobin solution which is substantially free of stroma and other contaminants.

For purposes of this invention, the term cross-linked means the chemical emplacement of molecular "bridges" onto or into a hemoglobin molecule, or between molecules, with the purpose of altering the shape, size, function or physical characteristics of the molecule. Tetramer refers to hemoglobin molecules having a molecular weight of about 64 kD; that is, the term refers to both native and intramolecularly cross-linked hemoglobin molecules. The term essentially tetramer-free denotes the level of purity with respect to tetramer contamination at which certain biological responses to tetramer administered into a mammal are no longer of clinical concern. Preferably, the solution contains no more than about 2.0% free tetramer as measured by standard HPLC methods, based on the weight of total hemoglobin. Particularly preferred products contain less than about 1.0% free tetramer.

Preferably, the hemoglobin solution of the present invention is a polymerized, hemoglobin solution essentially free of tetrameric hemoglobin and various contaminants, is physiologically acceptable as well as therapeutically and clinically useful. The product has reversible oxygen binding capacity which is necessary for oxygen transport properties. Most notably, the product demonstrates good oxygen loading and unloading characteristics in usage which correlates to having an oxygen-hemoglobin affinity ($P_{50}$) similar to whole blood. The product shows a high affinity for binding oxygen in the capillaries through the lungs and then adequately releases oxygen to the tissues in the body. The product also does not require compatibility studies prior to use with the recipient. An example of the preparation of such a hemoglobin solution is described in U.S. Pat. No. 6,498,141, the disclosure of which is incorporated herein by reference in its entirety.

The packaged hemoglobin solution of the present invention is substantially oxygen free throughout the shelf life of the solution. While it is most preferred that the hemoglobin solution contain absolutely no oxygen, it is expected that a small amount of oxygen will be present in the solution, such as oxygen introduced into the solution as part of the manufacturing or packaging processes. Further, it is expected that, under normal storage conditions, oxygen will penetrate the flexible package containing the hemoglobin solution. Accordingly, the hemoglobin solution is substantially oxygen free when the amount of oxygen introduced into the solution does not effect the clinical usefulness of the solution.

One measurement of oxygenation of the packaged hemoglobin solution is the oxyhemoglobin concentration expressed as the percentage of the total hemoglobin that is bound with oxygen. In the substantially oxygen free solution, oxyhemoglobin concentration is less about 15% during production and packaging. The clinical usefulness of the hemoglobin solution is compromised when oxygen present in solution causes the oxidation of the hemoglobin in the solution to methemoglobin such that the methemoglobin concentration exceeds about 8% expressed as the percentage of total hemoglobin that has been oxidized. It is preferred that the concentration of methemoglobin in solution is less than about 8%, more preferably less than about 5.0%.

The invention provides for several methods of preventing the oxygenation of the hemoglobin solution. First, the container for the hemoglobin solution may be a substantially oxygen-impermeable package such as a multi-layer polymeric film which allows for the transparency, flexibility and strength required of containers for medical solutions. Also, the solution may contain one or more preservatives which reduce or consume $O_2$ in the solution, thereby preventing $O_2$ from oxidizing the hemoglobin. Further, the solution should be packaged under an inert gas or in a manner that maintains the atmospheric oxygen in the "head space" in the container to less than about 2 cc of residual $O_2$ per package.

A polymer film is substantially oxygen impermeable when the clinical usefulness of a hemoglobin solution, packaged in a container comprising the polymer film, is not diminished due to oxygen penetrating the film over the shelf life of the product under the appropriate storage conditions. Typically, the oxygen permeability of the polymer film will depend upon the type of materials used, the thickness of the materials and storage conditions (lower storage temperatures yield lower $O_2$ permeability). With regard to any one particular material, thicker materials are generally less flexible and less transparent than thinner materials. It has been found that the desired flexibility and transparency of the polymeric film may be achieved with a film having an oxygen permeability of 0.05 to about 0.30 $cc/m^2$ per 24 hours per atmosphere at about 5° C. and an external relative humidity of about 60%. This same container will have an oxygen permeability of about 0.15 to about 0.5 $cc/m^2$ per 24 hours per atmosphere at about 25° C. and an external relative humidity of about 60%.

Figure 1B:
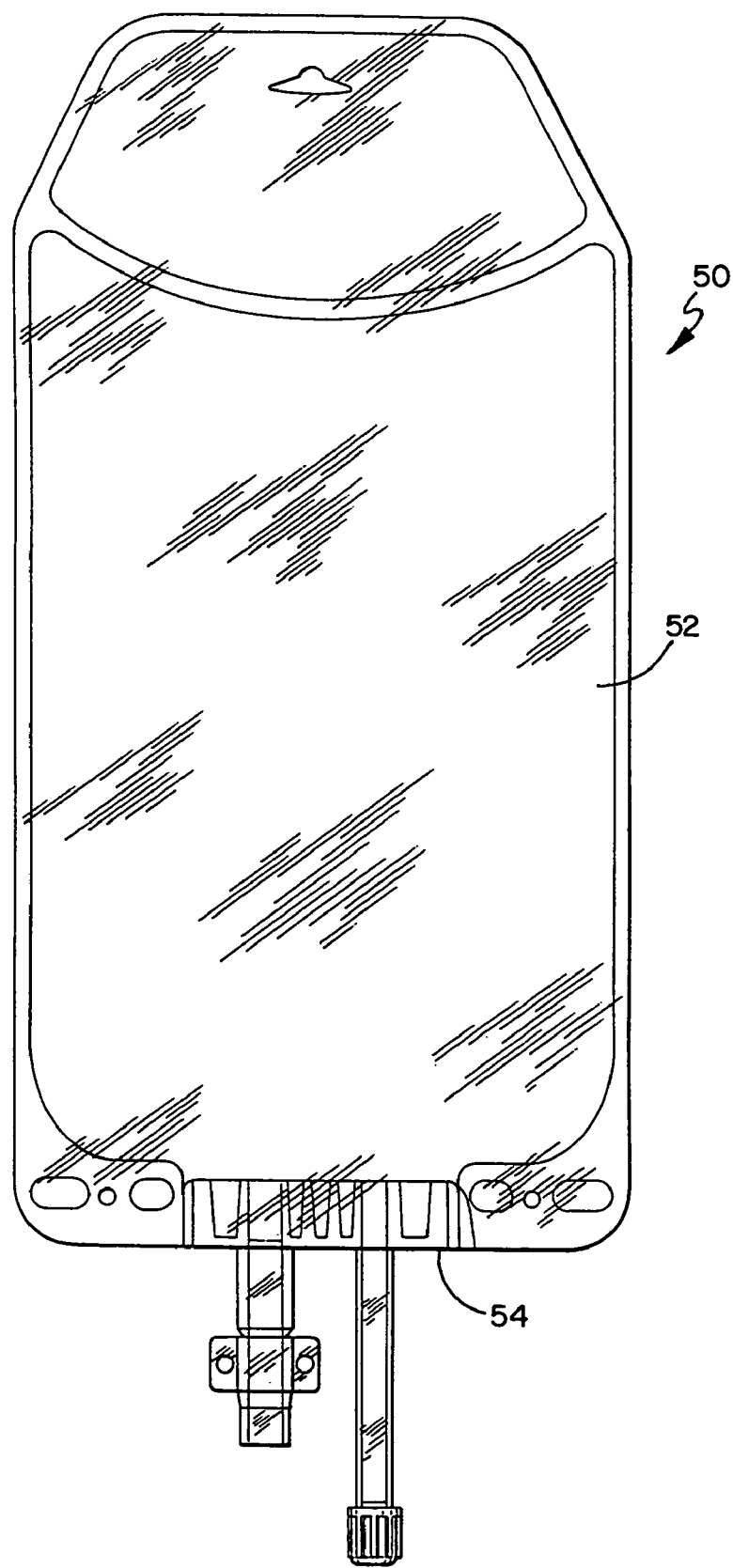

FIGS. 1A and 1B are diagrams illustrating preferred embodiments of the flexible container system 10, 50. The flexible container system includes the flexible container or bag 12, 52 and the fill/delivery interface or port 14, 54. The flexible container includes a multi-layer film 16, which is suitable for forming a flexible pouch. The requirements for a particular embodiment of the flexible container system are described in Table 1. The values provided in Table 1 are for a container system having a shelf life of a minimum of one year and stored within a temperature range of approximately 2–8° C.

While the flexible container should not require a secondary barrier for use as an oxygen and moisture barrier because the transmission rates through the primary multi-layer film are low enough to eliminate the need for a secondary barrier-type over wrap, a sealed transparent, protective secondary overwrap, or a hard clam shell type container, is preferred in order to minimize particulate accumulation on the container or primary packaging. In addition, the overwrap can house detailed label instructions and minimize the likelihood of physical damage caused by handling or tampering. The overwrap may be made from materials such as, but not limited to, polyethylene and polypropylene, or hardshell-type standard plastic materials such as high impact polystyrene, a metal oxide coated polyolefin (PE or PP), or BAREX® resins (BP Chemicals, Naperville, Ill.).

In addition to maintaining the hemoglobin solution in an oxygen impermeable package to preserve the solution, various additives may be used to prevent oxygenation and methemoglobin formation, and to maintain polymer stability. Stability of the polymer may be determined by measuring the extent of tetramer elaboration and the molecular weight distribution of hemoglobin polymers in the solution. It is expected that the solution will contain a minimum amount of tetramer following formulation. It is further expected that tetramer elaboration may occur over time during storage of the solution due to the breakdown of the polymer. The desired concentration of the 64 kD hemoglobin tetramer is determined by the volume of dosage and rate of infusion. In the present invention where it is desired to have a solution allowing for a high rate of infusion, the concentration of the 64 kD hemoglobin tetramer over the shelf life of the product is preferably less than about 2.0%, more preferably less than about 1.0%. Also, The preferred distribution of hemoglobin polymers is: 256 kD 49–74%; 192 kD 16–28%, 128 kD 9–23% as measured by HPLC.

It has been found that ascorbic acid has a significant stabilizing effect in terms minimizing hemoglobin conversion to oxyhemoglobin and methemoglobin. Ascorbic acid is a reducing agent that functions primarily as an electron carrier. In the hemoglobin solution, the ascorbic acid reduces $O_2$ present in the solution thereby preventing the $O_2$ from oxidizing the hemoglobin. It is expected that, throughout the shelf life of the hemoglobin solution, the ascorbic acid will be consumed as it reduces oxygen initially present in the solution and further reduces the oxygen that permeates the container. Accordingly, it is preferable that the amount of ascorbic acid added to the hemoglobin solution is sufficient to maintain the ascorbic acid concentration above about 0.2 g/L (as a factor of safety) over the shelf life of the product.

TABLE 1

| Parameter | Requirement | Conditions |
| --- | --- | --- |
| $O_2$ Transmission Rate ($O_2$TR) | Not More Than (NMT) 0.17 cc $O_2/m^2$ - 24 hours-atm and/or | 5° C., 60% relative humidity (RH), atm |
| | NMT 0.50 cc $O_2/m^2$-24 hours-atm | 25° C., 60% RH, atm |
| Water Vapor Transmission Rate (WVTR) | NMT 1.19 $g/m^2$ - 24 hours-atm | 5° C., 60% RH, atm |
| Residual $O_2$ Content | NMT 2 cc/container | |
| Particulate | NMT 3.0/ml 10 μm NMT 0.2/ml 25 μm | When filled at nominal volumes and tested per USP particulate test |
| Seal Strength - Burst Test (Restrained) | Not Less Than (NLT) 30 psig | Restrained, 1 inch gap |
| Sterility | SAL of $10^{-6}$ | Gamma irradiation - 25–35 kGy |
| Pyrogenicity | NMT 0.125 EU/ml | Limulus Amoebocyte Lysate Procedure |
| Container Closure Integrity Test | 10 psig | Compliant with PDA Technical Report No. 27, April 1998. |

Therefore, while concentrations of ascorbic acid as low as about 0.1 have been found to have the desired benefit of lowering methemoglobin concentrations in the solution, it is preferred that the initial concentration of ascorbic acid in the solution is in the range of about 0.25 to 1.0 g/L, preferably about 0.8 g/L to ensure a useful concentration of ascorbic acid remains in the solution over the shelf life of the product.

Glycine ($C_2H_5NO_2$) and dextrose are other preservatives that may be added to the hemoglobin solution to ensure the clinical usefulness of the solution. Glycine has been shown to have a significant stabilizing effect with regard to methemoglobin formation and glycine can effect high molecular weight polymer aggregation. Preferably, the concentration of glycine in the hemoglobin solution is in the range of 1–5 g/L. More preferably, the glycine concentration is about 3.5 g/L. Dextrose has been shown to have a stabilizing effect in regards to methemoglobin formation. In addition, the combination of glycine and dextrose has been shown to reduce tetramer elaboration.

The values and ranges used to describe the invention are desirable to attain the goals of the invention. However, it should be understood that small variations from these ranges may not substantially affect the performance of the hemoglobin solution. Therefore, the invention provides for a packaged hemoglobin solution having the described characteristics and the solution may vary from those characteristics to the extent that the clinical usefulness of the packaged hemoglobin solution in not compromised.

The flexible container fits in the standard equipment in an operating or emergency room such as, for example, a pressure infuser and/or warmer. Either manual "pressure cuffs" or automated infusers, such as a pressure infusion system H25 supplied by Level 1 Inc. (Rockland, Mass.) may be utilized. Medical solution containers need to have sufficient durability to remain leak-free during such procedures. Infusion of hemoglobin solutions may need to be performed as rapidly as possible in order to resuscitate patients in low blood flow states with dangerously low hemoglobin levels. For example, in certain medical applications infusion rates as high as approximately 350 ml/minute may be necessary in order to sustain life. Actual infusion rates are limited by, for example, the restricted orifice of a standard 18 gauge infusion needle, patient considerations, and tetramer levels of the solution. Average infusion rates shown in Table 2 correspond to an acellular hemoglobin solution, for example, POLYHEME® supplied in an I.V. bag for in-vivo intravenous (IV) infusion (Northfield Laboratories, Inc., Evanston, Ill.). The high infusion rates associated with this product are allowable because the 64 kD hemoglobin tetramer level of the solution is less than about 2%. The clinical administration of POLYHEME® may range from gravity-drip infusion to high-pressure driven rapid infusors.

TABLE 2

| Units | Volume/Unit (mL) | Time Interval (min) | Rate (mL/min) |
|---|---|---|---|
| 1 | 500 | 190 | 2.6 |
| 6 | 500 | 35 | 85.7 |
| 10 | 500 | 23 | 217.4 |
| 18 | 500 | 72 | 125.0 |
| 10 | 500 | 180 | 27.8 |

The polymeric film for packaging the hemoglobin solution is a thermoplastic material, generally in sheet or web form, having one or more layers of polymeric materials which may be bonded together by any suitable means well known in the art. The terms "polymer," "polymeric," and the like, unless specifically defined, generally include homopolymers, copolymers, terpolymers, and blends and modifications thereof.

As used herein, the term "olefin" refers to any one of a class of monounsaturated, aliphatic hydrocarbons of the general formula $C_nH_{2n}$, such as ethylene, propylene, and butene. The term may also include aliphatics containing more than one double bond in the molecule such as a diolefin or diene, e.g., butadiene.

"Polyolefin" refers to olefin polymers and copolymers, especially ethylene and propylene polymers and copolymers, and to polymeric materials having at least one olefinic comonomer, such as ethylene vinyl acetate copolymer and ionomer. Polyolefins can be linear, branched, cyclic, aliphatic, aromatic, substituted, or unsubstituted. Included in the term polyolefin are homopolymers of olefin, copolymers of olefin, copolymers of an olefin and a non-olefinic comonomer copolymerizable with the olefin, such as vinyl monomers, modified polymers of the foregoing, and the like. Modified polyolefins include modified polymers prepared by copolymerizing the homopolymer of the olefin or copolymer thereof with an unsaturated carboxylic acid, e.g., maleic acid, fumaric acid or the like, or a derivative thereof such as the anhydride, ester metal salt or the like. It could also be obtained by incorporating into the olefin homopolymer or copolymer, an unsaturated carboxylic acid, e.g., maleic acid, fumaric acid or the like, or a derivative thereof such as the anhydride, ester metal salt or the like.

The term "ethylene/alpha-olefin copolymer" means copolymers of ethylene with one or more comonomers selected from $C_3$ to $C_{20}$ alpha-olefins, such as 1-butene, 1-pentene, 1-hexene, 1-octene, methyl pentene and the like, in which the polymer molecules comprise long chains with relatively few side chain branches. These polymers are obtained by low pressure polymerization processes and the side branching which is present will be short compared to non-linear polyethylenes (e.g., LDPE, a low density polyethylene homopolymer). Ethylene/alpha-olefin copolymers generally have a density in the rage of from about 0.86 g/cc to about 0.94 g/cc. The term linear low density polyethylene (LLDPE) is generally understood to include that group of ethylene/alpha-olefin copolymers which fall into the density range of about 0.915 to about 0.94 g/cc. Sometimes linear polyethylene in the density range from about 0.926 to about 0.94 is referred to as linear medium density polyethylene (LMDPE). Lower density ethylene/alpha-olefin copolymers may be referred to as very low density polyethylene (VLDPE, typically used to refer to the ethylene/butene copolymers with a density ranging from about 0.88 to about 0.91 g/cc) and ultra-low density polyethylene (ULDPE, typically used to refer to the ethylene/octene copolymers).

In a preferred embodiment, the invention provides a hemoglobin solution packaged in a multi-layer film including an interior or product contact layer, which is inert and non-reactive with the solution contained in the flexible container. In addition, the interior layer is tacky enough for the contact surfaces to self-adhere to each other in order to minimize particulate contact and facilitate handling during the container manufacturing process. Further the inner layer protects the oxygen barrier layer from water vapor arising from the solution.

The preferred multi-layer film further includes an oxygen barrier layer. Further, the multi-layer film includes an exterior layer that protects the barrier layer from heat and humidity. As such, the exterior or outer layer protects the barrier layers from high welding temperatures during the bag making process as well as provides durability, printability and scuff resistance. Therefore, the barrier layer typically does not see temperatures above its melting point during the welding process in order to maintain the integrity of the film. The product contact layer melts only to the point which is required to self adhere. Thus, the temperature which the outer layer must withstand is dependent on the entire film structure and thicknesses and must be high enough to allow for adhesion between the interior two contact layers. The changes in temperature will vary depending on the number and types of layers in the film. Further, the melting temperatures of the contact layers are exceeded only for a short period of time to ensure the integrity of the bag weld as the contact layers have a lower melting temperature than the barrier and outside layers.

In one embodiment, the multi-layer film includes the following layers, in the following order, (1) a product contact layer made from an ethylene/propylene copolymer (EPC, PP/PE blend), (2) a tie layer comprising an EVA blend, (3) a layer of linear low density polyethylene (LLDPE), (4) another tie layer, (5) an oxygen barrier layer of EVOH, (6) another tie layer, (7) a layer of LLDPE, (8) another tie layer, and (9) an exterior or outside layer of polyester (PET).

In another embodiment, the multi-layer film comprises a linear low-density, polyethylene (product contact layer), a tie layer such as ethylene vinyl acetate (EVA), an EVOH layer (primary barrier layer), and an EVA layer (outside layer).

In another preferred embodiment, the multi-layer film includes the following layers in the following order: (1) an EVA product contact layer, (2) an EVA tie layer (preferably a different blend of EVA from the product contact layer), (3) a barrier layer made of polyvinylidene chloride-ethylene vinyl acetate (PVDC-EVA) composite, (4) an EVA tie layer, and (5) an outside layer of Low Density Polyethylene (LDPE). The second through the fifth layers are co-extruded. The first layer is laminated onto the second through fifth layers to form the multi-layer film.

Polymer films of this nature are available, for example, from Cryovac, Inc. (Duncan, S.C.), Stedim (Stedim, Aubange, France), and Solvay-Draka, Inc. (Commerce, Calif.).

In a particular embodiment of the packaged hemoglobin solution, the multi-layer film is co-extruded in a flat configuration or in an alternate embodiment it is co-extruded in a tubular film configuration. Where necessary, the exterior layer may also provide restraint of the interior layers to minimize curling of the outer edge of the co-extruded film during the bag manufacturing process. For example, in one particular embodiment, a nylon layer is laminated on the outer layer to provide a level of restraint.

Importantly, the film composite does not degrade physically or optically with the gamma irradiation required to meet sterility requirements of the packaged hemoglobin solution of the present invention. To ensure that the container is sterilized, it, in certain embodiments, is gamma irradiated or washed in a hydrogen peroxide or ethylene oxide bath. There is a benefit to gamma irradiation because it penetrates and sterilizes the entire film structure as well as eliminates any microbial bioburden on the interior layer of the flat film. Therefore, the preferred method of sterilization is typically gamma irradiation for this type of container in a range from approximately 25 kGy to 35 kGy. To ensure sterility, the medical containers are placed in a cardboard box and positioned on a pallet. In a preferred embodiment, dosimeters are used to monitor dose/sensitivity (parametric release). Another method of ensuring sterility includes strategically locating several vials of biological indicators on the pallet. If, when opened after sterilization and mixed with a trypcase-soy broth and no growth is recognized after incubation, the containers are certified as sterile and ready for aseptic fill of the blood substitute. This helps to ensure that the medical solution that cannot be terminally sterilized, as packaged in the medical solution containers, will be substantially free from microbial contamination. In a preferred embodiment, the packaging is improved by gamma-irradiation-induced-crosslinking (curing or vulcanizing) of the packaging film layers. Materials capable of crosslinking by gamma irradiation include polyethylene, ethylene copolymers, polyamides, polyesters and ethylene vinyl acetate. In one aspect of the invention, the various layers of the film are cross-linked within and between the layers. The film multi-layer is durable enough when manufactured into a container and filled with aqueous solution to withstand storage at low temperatures such as, for example, from about 2 to 8° C., and drops from a height of approximately 2 meters.

As can be appreciated by those having ordinary skill in this art, the packaged hemoglobin solutions of the present invention are not limited to containers with the layer structure described herein. Films having a fewer number of layers or a greater number of layers than that shown are included within the scope of the present invention. For example, additional layers, such as high density polyethylene, may be included in the film in order to increase the moisture barrier capabilities of the film if desired. Additional oxygen barrier layers may also be included if desired.

Multilayer films in accordance with the present invention are preferably cross-linked. Cross-linking increases the structural strength of the film at elevated temperatures and/or increases the force at which the material can be stretched before tearing apart, and may also improve the optical properties of the film. Any conventional cross-linking technique may be used. For example, electronic cross-linking may be carried out by irradiation.

In another embodiment, a method of the invention relates to a preserved deoxygenated hemoglobin solution that includes a deoxygenated hemoglobin solution and an oxygen barrier film primary package. In one embodiment, the oxygen barrier film primary package includes a transparent polymer film. The primary package has an oxygen permeability of less than about 0.17 cc $O_2$ per 1 square meter per 24 hours at atmosphere at approximately 5° C. and an external relative humidity of about 60%, within which the deoxygenated hemoglobin solution is sealed, thereby preserving the deoxygenated hemoglobin solution in an environment that is substantially free of oxygen. In another embodiment, the polymer film is a laminate-comprising a polyamide, for example, nylon, for the exterior layer.

The oxygen barrier film comprises suitable oxygen barrier materials such that the material has suitable oxygen barrier properties at 25° C. and ambient humidity, for example 60% relative humidity. In one preferred embodiment of the invention, the oxygen barrier material comprises a transparent polymer film having one or more layers. In a more particular embodiment, the film comprises a laminate of an outer polyolefin layer (such as polyethylene or polypropylene), an oxygen barrier layer and an inner polyolefin layer, wherein the inner layer is in contact with the contents of the package. The polyolefin's of the present invention can comprise copolymers of two or more monomers, wherein the monomers can be, for example, polypropylene, polyethylene, or polybutylenes. In another embodiment, other monomers such as ethylene vinyl acetate can be included in the copolymer. Depending upon the type of oxygen barrier layer, the laminate can optionally include a support layer. While not wishing to be bound by theory, the support layer facilitates the production of bags using an automated device. In a preferred embodiment, the support layer is a biaxially oriented material such as nylon.

In one embodiment, the outer polyolefin layer and the oxygen barrier layer are co-extruded. In a preferred embodiment, the outer polyolefin layer is medium density polyethylene and the oxygen barrier is ethylene vinyl alcohol.

In another embodiment of the invention, the oxygen barrier film comprises a co-extruded medium density polyethylene/ethylene vinyl alcohol layer (EVOH); a nylon layer; and a low-density polyethylene layer. Due to the brittleness of EVOH at low temperatures, the fill volume of the container system is adjusted with respect to the total volume of the container to optimize durability of the container during the standard drop test. In particular embodiments the ratio of the fill volume to the total volume of the container ranges from approximately seventy to seventy five percent (70–75%) fill volume for a one (1) liter container and eighty percent (80%) for a one-half (½) liter container. In a preferred embodiment, the ends of the container are rounded to closely simulate a circular continuous weld to avoid concentration of stresses in the container. Further, the EVOH barrier can be adjusted such as, for example, by controlling the thickness of the barrier to modify the oxygen transmission rates. In one aspect of the invention the EVOH barrier is about 20 micron thick.

As further described in Example 2 below, in another embodiment of the present invention, the oxygen barrier film comprises a PVDC structure which is laminated to an extruded EVA contact layer to generate a five-layer film (EVA tie layers and a low density polyethylene outside layer).

The inner and outer polyolefin layers may be vapor barriers protecting the humidity sensitive EVOH layer. The vapor barrier properties of either layer can be increased by increasing the thickness or crystallinity of the layer. Other suitable outer layers include, for example, linear low-density polyethylene, low-density polyethylene, high-density polyethylene, EVA or polyesters.

In another particular embodiment of the present invention, the oxygen barrier layer comprises an essentially oxygen-impermeable polymer, comprising a support material having a coating. In one embodiment, the support material can be, for example polyester or polyamide (such as nylon) and the coating can be, for example, silicon oxide ($SiO_x$) or other material, such as a metal oxide, that can be deposited onto the support to render it oxygen impermeable. In all embodiments, the oxygen barrier thickness can be adjusted to improve barrier characteristics.

In all embodiments, the exterior layer should be capable of adding durability such as, for example, puncture resistance to the container and provide the option for printing such as, for example, hot stamping a label on the container.

In a preferred embodiment, an overwrap is employed. As described above, the overwrap can be manufactured from a suitable material, such as polymer films, for example, polyester, polyethylene, or nylon, or a laminate, such as a foil laminate, for example, a silver or aluminum foil laminate. The overwrap may also be a rigid clam-shell type container such as those manufactured from by Alloyd Company (Dekalb, Ill.). The overwrap protects the container from damage caused by mishandling or tampering. It also provides protection against particulates and may function as a label sleeve for the primary container.

The primary package and the overwrap, if present, can be manufactured using a variety of configurations, including, but not limited to, vials, cylinders, and boxes. In a preferred embodiment, the primary package is in the form of a bag. A suitable bag can be formed by, for example, continuously bonding two sheets at the perimeters thereof to form a tightly closed, oxygen impermeable, construction having a fillable center. Where linear low, medium or high-density polyethylene is used as the inner layer of the material, the sheets can be sealed by heating under the appropriate conditions. It is well known in the art that polyethylene can be sealed against itself with heat under the appropriate conditions. It is well known in the art that parameters can be varied to obtain proper bonding of polyolefin surfaces of film, these parameters include temperature, pressure and time, wherein time is the duration of time the sheets are put under pressure and temperature. Typically, linear low-density polyethylene requires less heat and progressively higher density polypropylene requires progressively more heat. In addition, higher density polyolefin's typically tolerate higher pressure during the welding process. In general, if the pressure is excessive, for example, greater than 5 bar pressure, the heated material may be forced away from the area of contact, creating a weaker seal.

Figure 2:
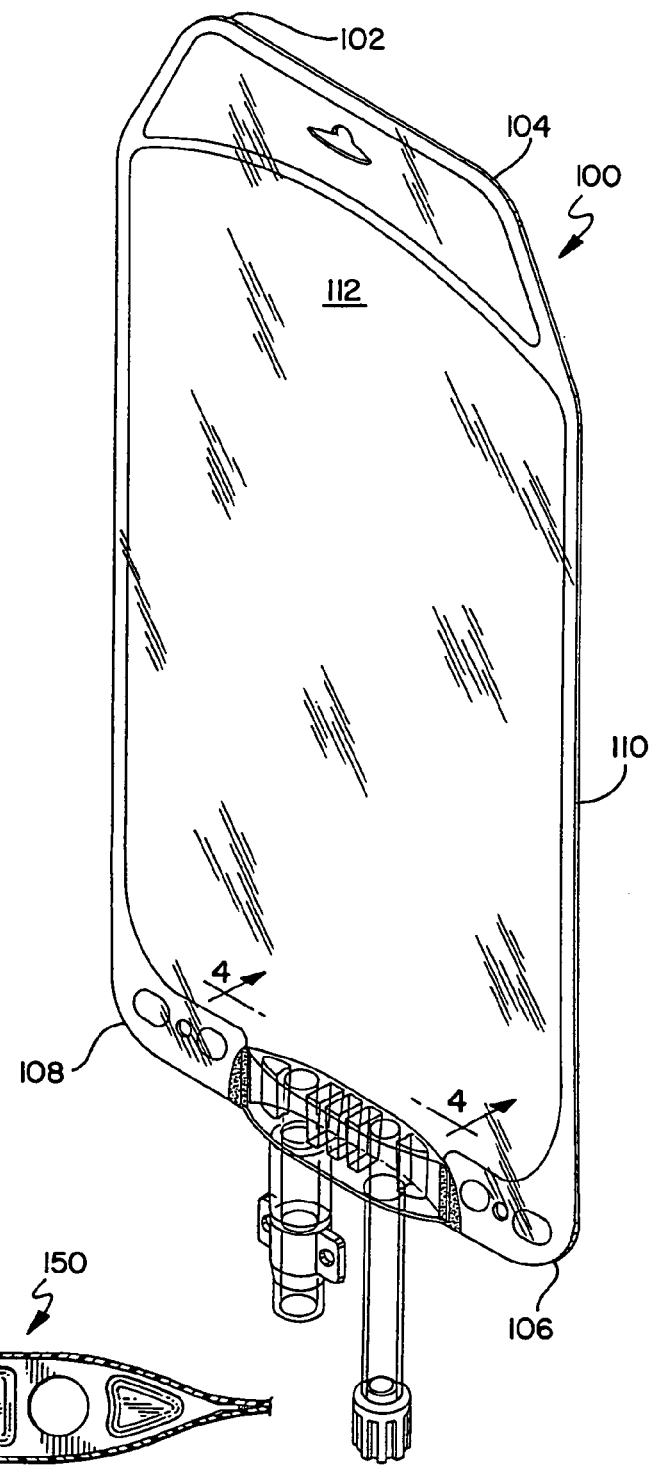
FIG. 2 is a diagram illustrating a perspective view of the flexible container system in accordance with the preferred embodiment of the present invention as illustrated in FIG. 1A.
Figure 5:
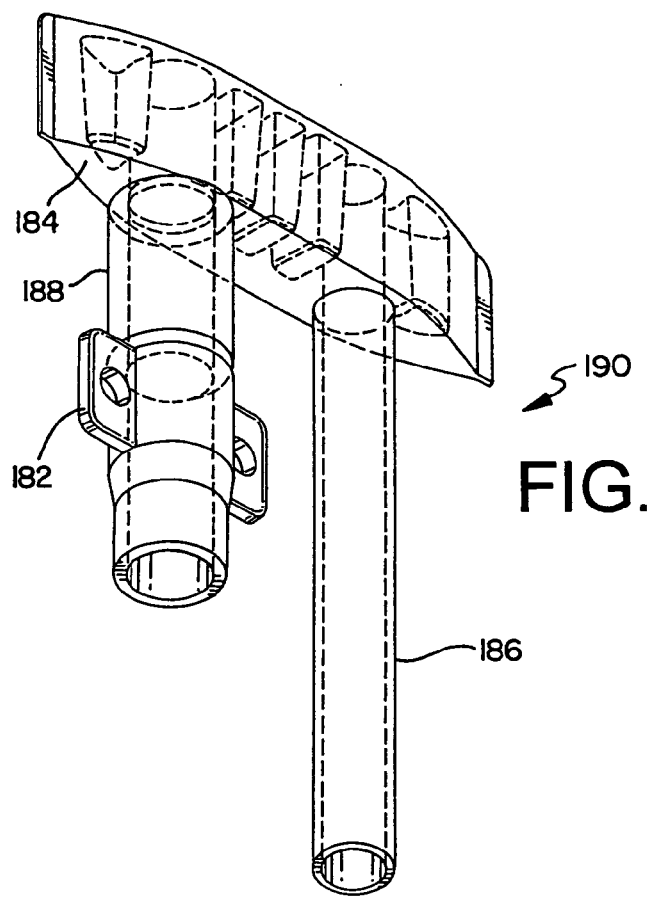
FIG. 5 is a perspective view looking upwardly at the bottom of the fill and/or delivery port in accordance with a preferred embodiment of the present invention.

FIG. 2 is a diagram illustrating a perspective view 100 of the flexible container system as illustrated in FIG. 1A in accordance with a preferred embodiment of the present invention. The ends 102, 104, 106, 108 of the container 110 are rounded to closely simulate a circular continuous weld to avoid concentration of stresses in the container. Further, in a particular embodiment, the headspace 112 in the container is minimized to reduce the residual oxygen content. In a particular embodiment, the residual oxygen content is less than approximately two-cubic centimeters (2 cc). FIG. 5 is a perspective view looking upwardly at the bottom of the fill and/or delivery port 190 in accordance with a preferred embodiment of the present invention.

The flexible container system includes an interface port for filling the flexible container with aqueous material and delivering the aqueous material. The interface ports are integral with the multi-film of the container system and in preferred embodiments are injection-molded. The interface ports can have a multitude of configurations such as, but not limited to, boat shaped ports (boat port), hard ports that simulate ports on a bottle, and saddle or face ports. A preferred embodiment of the invention has a boat port.

Figure 3:
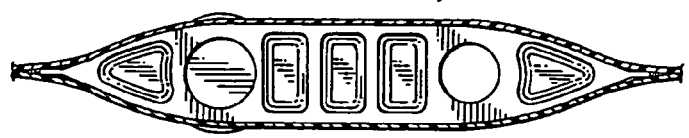
FIG. 3 is a cross-sectional view looking at the top of the fill and/or delivery port taken along line 3—3 of FIG. 1A in accordance with a preferred embodiment of the present invention.
Figure 4:
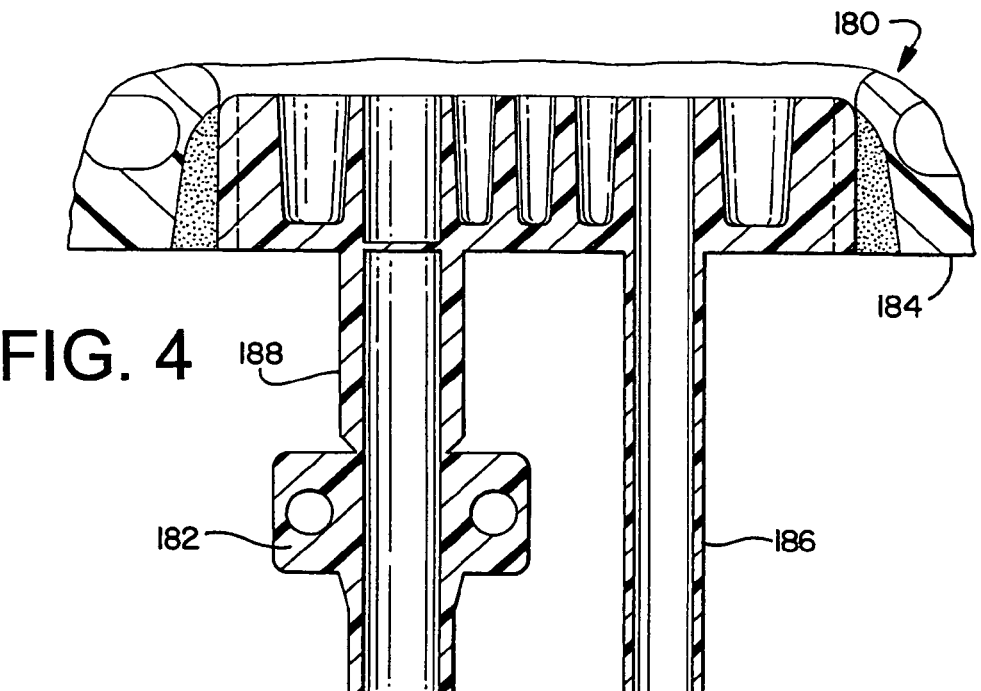
FIG. 4 is a longitudinal cross-section view taken along line 4—4 of FIG. 2 of the fill and/or delivery port in accordance with a preferred embodiment of the present invention.

FIG. 3 is a diagram illustrating a cross-sectional view looking at the top of the fill and/or delivery port 150 taken along the line 3—3 of FIG. 1A in accordance with a preferred embodiment of the present invention. FIG. 4 is a diagram illustrating a longitudinal cross-sectional view taken along line 4—4 of FIG. 2 of the fill and/or delivery port 180 in accordance with a preferred embodiment of the present invention. FIG. 5 is a perspective view looking upwardly at the bottom of the fill and/or delivery port 190 in accordance with a preferred embodiment of the present invention.

In a preferred embodiment, the diameter of the interface port is approximately 0.210±0.05 inches below an administration side membrane with, but not limited to, a range of 0.5 to 5 degrees draft or degrees of deflection. This diameter is compatible with the standard spike ports mentioned herein. A draft above the administration side membrane facilitates the gripping of the spike. The membrane thickness is approximately 0.02 inches at the spike. This dimension allows for ease in spiking. In addition, with materials such as the Ferro RxLoy polyolefin polymer resin, the membrane is compressible which facilitates the boat ports compatibility with all standard spikes. When the bag is under pressure during administration of the product, the boat port deforms to apply pressure to the spike, which eliminates the risk of the spike being expelled under pressures as high as approximately 1000 mm of Hg. In other embodiments, less elastic materials than the Ferro resin may require this membrane to be thinner to allow for ease in spiking.

In a preferred embodiment, the depth of the base 184 is in range of 8 mm to 12 mm. This provides for ease in automated insertion into film as it provides for tolerance. The depth from the top of the base 184 to the bottom of twist 182 is 0.65 inches. This eliminates the risk of puncturing the bag with the spike i.e., the tip of the spike terminates in the base of the boat port. In a particular embodiment, the width of base is approximately 0.32 inches. This width is optimized for all other dimensions including wall thickness of boat port stiffeners and administrative/fill diameters on base when using a boat port. This dimension is also important for minimizing residual oxygen in the container. In a particular embodiment, the tear area under the administration twist 182 is approximately=0.01 inches±0.001 inches. This dimension optimizes shear stress required using above referenced Ferro RxLoy material to remove the cap prior to spiking for infusion which complies with ergonomic requirements optimized for emergency room staff to remove the cap. In other embodiments using less elastic materials, the dimension of the tear area may be reduced to approximately 0.005 inches±0.001 inches to allow for the twist removal of cap. The top of the administration port is preferably sealed to minimize potential for particulate and microbial contamination during storage or subsequent use in the emergency or operation room. Further, in a particular embodiment, the fill tube inside diameter is approximately 0.2 inches and thus is compatible with most standard filling needles. In addition, stiffeners may be included in the interface port to minimize level of sink and maximize the backing strength during a manufacturing process such as, for example, welding.

The inner diameter of the administration port is determined to optimize interfacing with or "gripping" of all potential spikes used in a medical environment. It utilizes the compressibility of the spike membrane for fitting all spike diameter variability. The administration port twist 182 is used to protect the spike membrane from both particulates and unintended spiking and is optimized for ease of removal and disposal in an operating room. The height of the administration port is designed to allow penetration of the membrane with the spike, but avoids scraping of the film i.e., the spike opening penetrates the membrane layer. The fill tube 186 of the administration port 180 has a length and wall thickness optimized to fit existing filling machine needles. The diameter of the administration or delivery side 188 of the interface port is compatible with commonly used spikes including, but not limited to, IVAC Administration Set— 28034 E, Level 1 spike, D-50 or D-100, and standard spikes provided by Baxter, Fenwal, and Travenol spike sets. Preferably the elasticity of the interface port material is that similar to of the Ferro RxLoy polyolefin polymer resin or equivalents thereof which optimizes conformity to common spikes. The resin is compatible with the product contact layer of the film. A particular embodiment includes only one administration port as venting is not required and only single spiking is acceptable. In a preferred embodiment, the length of the fill tube 186 may be cut down to match an administration port height in the future for an automated fill machine.

The width of the interface port such as, for example, a boat port in a particular embodiment and the opening of the film are critical parameters to minimize the amount of atmosphere allowed into the container during filling. Preferably residual $O_2$ in the contaner is 2 cc or less. The base of the boat port depth is designed for ease in automated placement in flat or tubular film. The stiffener design at the base of the boat port is optimized for mold fill and to eliminate sink i.e., maintains consistency of piece thickness for uniform cooling. The flash at both ends of the base is utilized for welding surface to film. The interface ports are optimized for ease in mold removal to avoid sticking to the injection-molded tool. In one embodiment, the overall dual-tube boat port assembly is designed as a one-piece injection-molded filling/administering port assembly and is easily welded into the container by heat, thus not requiring the use of adhesives.

Figure 6:
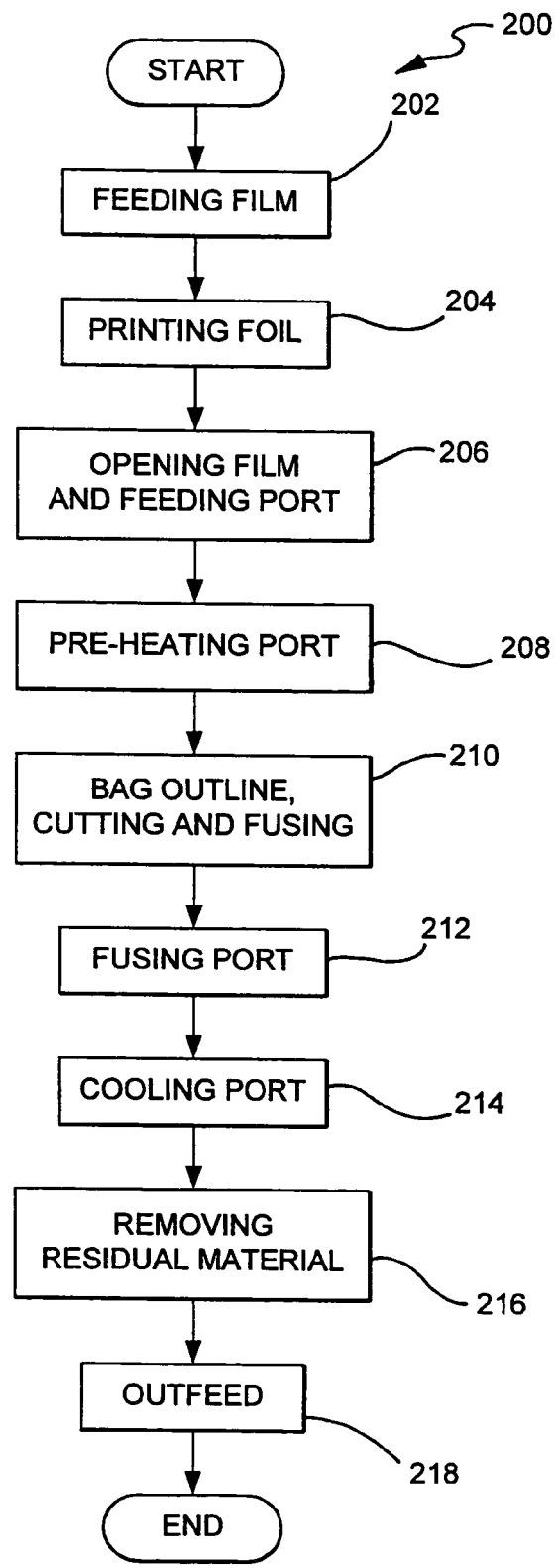
FIG. 6 is a flowchart of the method of fabrication of the flexible container system in accordance with a preferred embodiment of the present invention.

FIG. 6 is a flowchart illustrating the method of manufacturing and/or assembling the flexible container system in accordance with a preferred embodiment of the present invention. The automated method 200 of manufacturing the flexible container system includes procedure 202 of feeding the film into the manufacturing apparatus. In a preferred embodiment, the automatic film feeding is accomplished by a reeling frame. The step-wise and even feed motion is realized by an electric motor drive. The film is maintained in tension by utilizing compensating rollers and then stepwise feeding to the operation subsystems. The next procedure 204 in the process is the printing station subsystem. A hot-foil printing device is used to accomplish a full-face print. In a preferred embodiment, print temperature, time, pressure and tolerances are adjustable parameters. An automatic print foil controller ensures that the machine alarms and stops, if the foil is at the end or torn off. A second hot-foil printing device can be installed if necessary. At procedure 206, a film opener and port feeding subsystem is present. By means of a machined knife the film layers are separated within the headspace in order to form an opening. In a particular embodiment, interface or fill/delivery ports are automatically fed through a preloaded, spring-loaded cartridge onto a linear transport system, which loads the dual-tube boat ports into the machine in a linear manner. They are put into port receptacles manually or on a feeding chain, which positions the ports in between the opened film layers. The entire area comprising the insertion of the dual-tube boat port is contained under a unidirectional flow hood to minimize the presence of particles entrained in the final container.

A port pre-heating subsystem is the next procedure 208 in the method 200. In a particular embodiment, port pre-heating is accomplished by a contact heating system. This subsystem incorporates a welding temperature controller to control the minimum and maximum temperature, which alarms and stops the machine if the temperature is not within the specific tolerance.

In procedure 210, a bag out-line, port tack welding, and outline cutting subsystem is the next process accomplished. In this subsystem the bag outline is welded, the interface port is tack-welded and the bag outline is cut. The sealing operation is accomplished by movable welding dies in connection with the thermal welding device. Welding time, pressure and temperature include some of the parameters that are adjustable and therefore are controlled and recorded. This subsystem incorporates a minimum, and/or maximum welding temperature control, which stops the machine if the temperature gets out of the allowed range. A port welding subsystem is the next process procedure 212. Port welding is accomplished by a contact heat-sealing system in a particular embodiment. This subsystem also incorporates a minimum and/or maximum welding temperature control, which stops the machine if the temperature gets out of the allowed range. At the port cooling system per procedure 214, the port welds are air-cooled.

The following Table 3 provides exemplary ranges to optimize weld, pressure and residence time settings for pouch weldings, port welding and label printing for an exemplary film. The top and bottom dies are controlled separately.

TABLE 3

| Port material | Ethylene - propylene co-polymer resin | | min. | max. |
|---|---|---|---|---|
| Printing station | Temperature printing station | 160° C. | 155° C. | 165° C. |
| | Printing time | 0.5 sec. | 0.5 sec. | 0.5 sec. |
| | Pneumatic pressure | 2.5 bar | 2.0 bar | 3.0 bar |
| Contour welding and separation station | welding temperature | 136° C. | 131° C. | 141° C. |
| | Welding time | 2.7 sec | 2.7 sec | 2.7 sec |
| | Pneumatic pressure | 3.5 bar | 3.0 bar | 4.0 bar |
| Pre heating station | Temperature port preheating | 150° C. | 145° C. | 155° C. |
| | time preheating | 4.0 sec | 4.0 sec | 4.0 sec |
| Port welding 1 | temp. welding 1 top | 150° C. | 145° C. | 155° C. |
| | temp. welding 1 bottom | 150° C. | 145° C. | 155° C. |
| | Welding time | 2.5 sec | 2.5 sec | 2.5 sec |
| | Pressure | 6.0 Bar | 5.0 Bar | 7.0 Bar |
| Port welding 2 | temp. welding 2 top | 30° C. | 25° C. | 35° C. |
| | temp. welding 2 bottom | 30° C. | 25° C. | 35° C. |
| | Welding time | 1.5 sec | 1.5 sec | 1.5 sec |
| | Pressure | 6.0 Bar | 5.0 Bar | 7.0 Bar |

At the scrap material removal system per procedure 216, the scrap material of the finished bags is automatically removed by a gripper. The finished bags are placed onto a belt conveyor at the outfeed subsystem per procedure 218.

FIGS. 7 and 8 are side and top views, respectively illustrating the assembly process 250 for manufacturing the flexible container system in accordance with a preferred embodiment of the present invention. The assembly process 250 includes different subsystems and stations of machines to accomplish the method 200 to manufacture the container system described with respect to FIG. 6. The film is fed and the printing of the film occurs at printing station 254 or alternatively at station 256. The film is then transferred using station 252 to the film opener and port feeding station 258. The process then moves to the pre-heating station 260. The assembly process 250 then moves to the bag outline, welding and shearing station 262. The next station encountered in the process is the port welding station 264 followed by the port cooling station 266. The assembly process then moves to the removal of residual material station 268. The container system is obtained at the outfeed belt 270.

In a preferred embodiment, the blood substitute is packaged under an atmosphere, which is substantially free of oxygen. Examples of suitable atmospheres include nitrogen, argon and helium. In a further preferred embodiment, the film forms the flexible container system with a boat port interface. In another preferred embodiment, the film forms the flexible container system and includes standard medical tubing connected thereto by way of medical adhesives.

EXAMPLES

Example 1

A multi-layer film was tested for oxygen permeability when used as a primary package for the hemoglobin solution of the present invention. The multi-layer film includes the following layers, in the following order, (1) a product contact layer made from an ethylene/propylene copolymer (EPC, PP/PE blend), (2) a tie layer comprising an EVA blend, (3) a layer of linear low density polyethylene (LL-DPE), (4) another tie layer, (5) an oxygen barrier layer of EVOH, (6) another tie layer, (7) a layer of LLDPE, (8) another tie layer, and (9) an exterior or outside layer of polyester (PET).

Partially formulated lots of the stroma free, polymerized, pyridoxylated hemoglobin solution were essentially prepared as described in U.S. Pat. No. 6,498,141. The solution was packaged in 0.5L bags fabricated from the multi-layer film described in this Example. The units were tested at 3 months intervals for 18 months at 2–80° C. (Table 4), or for 9 months at 23–280° C. (Table 5), to determine total hemoglobin (g/dL), percent oxyhemoglobin (% $O_2$) and percent methemoglobin (% MetHb). Samples were diluted, and brought to constant temperature prior to measurement. Total hemoglobin, oxyhemoglobin and methemoglobin were determined using a IL 482 CO-Oximeter, Instrumentation Laboratories Inc, according to the direction of the manufacturer.

TABLE 4

| | | 2–8° C. Data | | |
|---|---|---|---|---|
| Time | Lot | THb (g/dL) | % $O_2$Hb | % MetHb |
| 0 Time | CF903 | 10.1 | 2.6 | 2.6 |
| | CF905 | 10.0 | 2.6 | 2.0 |
| | CF906 | 10.0 | 3.8 | 4.2 |
| 3 mo. | CF903 | 10.1 | 2.8 | 1.6 |
| | CF905 | 10.2 | 3.7 | 1.5 |
| | CF906 | 10.0 | 3.2 | 1.8 |
| 6 mo. | CF903 | 10.1 | 3.6 | 1.5 |
| | CF905 | 10.0 | 3.8 | 1.4 |
| | CF906 | 10.0 | 3.3 | 1.6 |
| 9 mo. | CF903 | 10.1 | 3.7 | 1.7 |
| | CF905 | 10.3 | 3.2 | 1.2 |
| | CF906 | 10.0 | 3.3 | 2.0 |
| 12 mo. | CF903 | 10.2 | 3.3 | 1.7 |
| | CF905 | 10.3 | 4.3 | 1.4 |
| | CF906 | 10.1 | 3.4 | 1.5 |
| 15 mo. | CF903 | 10.2 | 3.3 | 2.1 |
| | CF905 | 10.2 | 3.6 | 1.5 |
| | CF906 | 10.0 | 3.9 | 1.8 |
| 18 mo. | CF903 | 10.2 | 4.3 | 2.2 |
| | CF905 | 10.3 | 5.4 | 2.0 |
| | CF906 | 10.2 | 3.1 | 1.6 |

TABLE 5

| | | 23–27° C. Data | | |
|---|---|---|---|---|
| Time Point | Lot | THb (g/dL) | % $O_2$Hb | % MetHb |
| 0 Time | CF903 | 10.1 | 2.6 | 2.6 |
| | CF905 | 10.0 | 2.6 | 2.0 |
| | CF906 | 10.0 | 3.8 | 4.2 |
| 3 mo. | CF903 | 10.2 | 4.8 | 2.6 |
| | CF905 | 10.2 | 3.5 | 2.4 |
| | CF906 | 10.0 | 4.3 | 2.7 |
| 6 mo. | CF903 | 10.3 | 3.7 | 3.7 |
| | CF905 | 10.1 | 3.7 | 2.7 |
| | CF906 | 10.0 | 3.3 | 3.7 |

Example 2

In a test similar to Example 1, the hemoglobin solution was packaged in a multi-layer film having an oxygen barrier of a PVDC-EVA composite. This multilayer film includes the following layers in the following order: (1) a product contact layer made of EVA, (2) an EVA a tie layer having a different blend of EVA from the product contact layer, (3) a barrier layer made of PVDC-EVA composite, (4) an EVA tie layer, and (5) an outside layer of Low Density Polyethylene (LDPE). The second through the fifth layers was co-extruded. The first layer was laminated onto the second through fifth layers to form the multi-layer film used in this example.

Units were prepared and tested as in Example 1 except the bags were fabricated from the barrier film described in this Example. Table 6 is the results of testing at 2–8° C. and Table 7 is the results at 23–28° C.

TABLE 6

2–8° C. Data

| Time | Lot | THb (g/dL) | % $O_2$Hb | % MetHb |
|---|---|---|---|---|
| 0 Time | CE901 | 9.9 | 3.6 | 2.2 |
| | CE902 | 10.0 | 4.0 | 2.2 |
| | CD904 | 10.0 | 2.9 | 2.1 |
| 3 mo. | CE901 | 10.0 | 4.4 | 1.8 |
| | CE902 | 10.1 | 3.1 | 1.5 |
| | CD904 | 10.1 | 3.7 | 1.8 |
| 6 mo. | CE901 | 10.1 | 3.5 | 1.7 |
| | CE902 | 10.0 | 3.6 | 1.5 |
| | CD904 | 10.0 | 4.3 | 1.4 |
| 9 mo. | CE901 | 10.0 | 4.1 | 1.8 |
| | CE902 | 10.0 | 3.6 | 1.4 |
| | CD904 | 10.2 | 3.5 | 2.7 |
| 12 mo. | CE901 | 10.1 | 3.0 | 1.6 |
| | CE902 | 10.2 | 3.1 | 1.3 |
| | CE901 | 9.9 | 2.7 | 1.7 |
| 15 mo. | CE901 | 10.0 | 3.3 | 2.4 |
| | CE902 | 10.0 | 3.1 | 1.7 |
| | CD904 | 10.1 | 3.4 | 2.4 |
| 18 mo. | CE901 | 10.1 | 3.4 | 1.6 |
| | CE902 | 10.1 | 3.6 | 1.3 |
| | CD904 | 10.1 | 4.3 | 2.1 |

TABLE 7

23–27° C. Data

| Time Point | Lot | THb (g/dL) | % $O_2$Hb | % MetHb |
|---|---|---|---|---|
| 0 Time | CE901 | 9.9 | 3.6 | 2.2 |
| | CE902 | 10.0 | 4.0 | 2.2 |
| | CD904 | 10.0 | 2.9 | 2.1 |
| 3 mo. | CE901 | 10.1 | 3.4 | 2.8 |
| | CE902 | 10.1 | 1.9 | 2.8 |
| | CD904 | 10.2 | 3.8 | 3.5 |
| 6 mo. | CE901 | 10.1 | 3.5 | 4.0 |
| | CE902 | 10.2 | 3.4 | 5.0 |
| | CD904 | 10.0 | 3.4 | 3.7 |

Example 3

The effects of ascorbic acid on oxyhemoglobin and methemoglobin levels and tetramer elaboration were measured over time. Partially formulated units of the stroma free, polymerized, pyridoxylated hemoglobin solution were essentially prepared as described in WO 97/35893. Glycine and dextrose were added at 1.75 and 5.0 g/L, respectively. No ascorbic acid was added.

For testing at recommended storage conditions (2–8° C.), units were packed in one liter bags fabricated from the barrier film described in Example 2. Two weeks following packaging, units were doped with 0.45M ascorbic acid to the desired concentration through a 0.2 µm filter using aseptic techniques, mixed thoroughly by hand and stored at 2–8° C. Upon the addition of ascorbic acid (T=0 days) and at intervals thereafter measurements of oxyhemoglobin and methemoglobin were determined using a IL 482 CO-Oximeter according to the direction of the manufacturer (Tables 8 and 9). Samples were diluted, hemolyzed and brought to constant temperature prior to measurement. In addition, at T=0 and at the various intervals described in Table 10, ascorbic acid levels were determined by HPLC using an HP1100 Chemstation (Hewlett-Packard). In these same samples, tetramer elaboration was measured as % 64 kD tetramer by HPLC (Table 11).

Units packaged for highly stressed storage conditions were placed in 1 gallon jars purged with nitrogen gas and sealed with TEFLON® PTFE lined closures. Glass jars were used to eliminate the effects of oxygen permeation of the flexible container at high temperatures. Each jar also contained oxygen-absorbing packets to remove any residual atmospheric oxygen from the purge and seal procedure. At the time of filling of the jars, ascorbic acid at the desired concentrations was added.

TABLE 8

Methemoglobin concentration (% MetHb) at 2–8° C. with varying starting ascorbic acid (A.A.) concentrations

| Sample # (A.A. conc.) | 0 days | 3 days | 7 days | 14 days | 27 days | 55 days | 182 days |
|---|---|---|---|---|---|---|---|
| 1 (0 g/L) | 3.6 | 5.0 | 6.2 | 9.1 | 11.1 | 15.6 | 27.0 |
| 2 (0.25 g/L) | 5.0 | 5.5 | 5.8 | 3.9 | 3.6 | 4.1 | 11.8 |
| 3 (0.5 g/L) | 4.8 | 5.6 | 3.4 | 3.0 | 3.2 | 4.0 | 5.0 |
| 4 (0.75 g/L) | 4.7 | 3.6 | 3.2 | 3.4 | 2.8 | 3.2 | 3.6 |
| 5 (1.0 g/L) | 4.4 | 4.0 | 3.4 | 2.8 | 2.6 | 3.0 | 4.2 |

TABLE 9

Oxyhemoglobin concentration (% $O_2$Hb) at 2–8° C. with varying starting ascorbic acid (A.A.) concentrations

| Sample # (A.A. conc.) | 0 days | 3 days | 7 days | 14 days | 27 days | 55 days | 182 days |
|---|---|---|---|---|---|---|---|
| 1 (0 g/L) | 12.6 | 12.6 | 12.2 | 11.6 | 17.1* | 10.2 | 10.7 |
| 2 (0.25 g/L) | 13.0 | 6.7 | 3.6 | 3.3 | 3.6 | 3.2 | 7.5 |
| 3 (0.5 g/L) | 13.2 | 3.9 | 3.0 | 3.6 | 3.6 | 3.2 | 5.2 |
| 4 (0.75 g/L) | 13.0 | 3.2 | 4.0 | 3.7 | 3.3 | 3.4 | 4.0 |
| 5 (1.0 g/L) | 12.8 | 3.2 | 3.0 | 2.6 | 2.9 | 2.9 | 3.6 |

*This data point was considered erroneous based on the results of other time points and was not used in data analysis.

TABLE 10

Ascorbic Acid concentration (g/L) at 2–8° C. with varying starting ascorbic acid (A.A.) concentrations

| Sample # (A.A. conc.) | 0 days | 3 days | 7 days | 14 days | 27 days | 55 days | 182 days |
|---|---|---|---|---|---|---|---|
| 1 (0 g/L) | 0 | 0 | 0 | 0 | 0 | 0 | 0 |
| 2 (0.25 g/L) | 0.260 | 0.191 | 0.152 | 0.130 | 0.147 | 0.123 | 0 |
| 3 (0.5 g/L) | 0.505 | 0.371 | 0.350 | 0.379 | 0.364 | 0.322 | 0.168 |
| 4 (0.75 g/L) | 0.745 | 0.644 | 0.557 | 0.596 | 0.579 | 0.584 | 0.456 |
| 5 (1.0 g/L) | 1.036 | 0.898 | 0.856 | 0.877 | 0.875 | 0.860 | 0.615 |

TABLE 11

Tetramer concentration (% Tetramer) at 2–8° C.
with varying starting ascorbic acid (A.A.) concentrations

| Sample # (A.A. conc.) | 0 days | 3 days | 7 days | 14 days | 27 days | 55 days | 182 days |
|---|---|---|---|---|---|---|---|
| 1 (0 g/L) | 0.366 | 0.414 | 0.464 | 0.556 | 0.685 | 0.861 | 1.42 |
| 2 (0.25 g/L) | 0.372 | 0.440 | 0.463 | 0.512 | 0.544 | 0.625 | 0.904 |
| 3 (0.5 g/L) | 0.376 | 0.428 | 0.450 | 0.487 | 0.527 | 0.596 | 0.800 |
| 4 (0.75 g/L) | 0.376 | 0.424 | 0.440 | 0.486 | 0.521 | 0.582 | 0.760 |
| 5 (1.0 g/L) | 0.366 | 0.424 | 0.451 | 0.478 | 0.511 | 0.584 | 0.733 |

Similar measurements (except for ascorbic acid) were taken for samples packaged for highly stressed conditions (glass jars) and stored at 40° C. Similar trends for % MetHb, % O2, and % Tetramer were identified.

Example 4

The effects of glycine and dextrose on the hemoglobin solution were studied to determine the optimum concentrations of these additives for long-term solution stability. Stroma-free, polymerized, pyridoxylated hemoglobin was essentially prepared as described in U.S. Pat. No. 6,498,141. Ascorbic acid was added at 0.8–1.1 g/L. In batch NA803, no sodium lactate was added and pH was adjusted with HCl to 9.12–8.82. In batch NF803, the final pH (no adjustment) was 8.38 and sodium lactate was added. It is not expected that the presence of sodium lactate in batch NF803 has an effect on the results of this study.

Following formulation, the solution was packaged in one-liter bags fabricated from the multi-layer film according to Example 2 for those units were tested under recommended storage conditions, or in glass jars as described in Example 3 for testing at highly stressed storage conditions. Units were spiked with additives as indicated in the following Tables 12–14, mixed thoroughly. Measurements were conducted as described in Example 1.

Table 12 shows that glycine and dextrose have a minor stabilizing effect on % MetHb concentration after eight weeks with samples stored under recommended conditions (2–8° C.). Similar results (not shown) were obtained when samples with glycine and dextrose (separately) were subjected to stressed conditions, but no significant difference was observed when under such conditions with an increase of glycine concentration from 1.75 g/L to 3.5 g/L.

TABLE 12

% MetHb Levels
Batch NA803 (2–8°)

| Sample | Time (wks.) | % MetHb |
|---|---|---|
| No Additives | 0 | 4.0 |
| 1.75 g/L Glycine | 8 | 3.4 |
| 5.00 g/L Dextrose | 8 | 3.7 |
| No Additives | 8 | 4.7 |

Table 13 shows that glycine had a stabilizing effect on the aggregation of high molecular weight polymers (polymers having over 5 tetramer units; 320+Kd) under stressed conditions. Further data (not shown) indicates that the stabilizing effect increases with dose escalation from 1.75 g/L to 3.5 g/L. However, dextrose had an opposite effect.

TABLE 13

Molecular Weight Distribution
Batch NA803 (40° C.) Stressed

| | | % Polymer Species | | | |
|---|---|---|---|---|---|
| Sample | Time (wks.) | 128K | 192K | 256K | 320 + K |
| 1.75 g/L Glycine | 0 | 23.6 | 28.2 | 47.2 | 0 |
| | 4 | 22.2 | 23.7 | 17.6 | 33.9 |
| | 8 | 21.2 | 22.3 | 18.2 | 35.3 |
| 5.00 g/L Dextrose | 0 | 23.6 | 28.2 | 47.2 | 0 |
| | 4 | 20.8 | 21.9 | 17.8 | 37.1 |
| | 8 | 29.8 | 15.7 | 12.6 | 39.1 |
| No Additive | 0 | 23.6 | 28.2 | 47.2 | 0 |
| | 4 | 21.9 | 23.2 | 17.3 | 35.1 |
| | 8 | 20.9 | 21.7 | 17.6 | 37.0 |

It was determined that changes in the pH within the range of 7.9 to 9.0 had pH had no effect on methemoglobin formation, tetramer levels or molecular weight distribution under highly stressed storage conditions.

Table 14 suggests a slight increase in tetramer elaboration associated with glycine under highly stressed storage conditions and that the elaboration increases with dose escalation from 1.75 g/L to 3.5 g/L.

TABLE 14

% Tetramer as a Function of Glycine or Dextrose
Batch NF803 (40° C.)

| Sample | T = 0 | T = 8 wks. |
|---|---|---|
| No additive | 0.2 | 1.9 |
| Glycine (1.75 g/L) | 0.2 | 2.0 |
| Glycine (3.50 g/L) | 0.2 | 2.5 |
| Dextrose (2.5 g/L) | 0.2 | 1.7 |
| Dextrose (5.0 g/L) | 0.2 | 2.0 |

Example 5

The optimization of combinations of glycine and dextrose was determined for experimental units packaged for highly stressed conditions (glass jars, see example 3). Table 15 shows the formulation additives for two samples otherwise prepared as described for Example 3. In this study, one sample was formulated to minimize tetramer elaboration and one sample was formulated to minimize high molecular weight polymer aggregation.

TABLE 15

Batch NF803

| Sample | Dextrose (g/L) | Glycine (g/L) | PH |
|---|---|---|---|
| Minimum Tetramer Elaboration | 2.50 | 3.50 | 8.4–8.6 |
| Minimum High M.W. Aggregation | 0 | 5.00 | 8.4–8.6 |

Table 16 shows that the Minimum High M.W. sample (glycine only) had a lower % MetHb at all times than the Minimum Tetramer Elaboration sample.

TABLE 16

% MetHb Over Time: NF803

| Sample | Time = 0 | T = 2 wks. | T = 4 wks. | T = 8 wks. |
|---|---|---|---|---|
| Minimum Tetramer Elab. | 3.5 | 2.1 | 2.3 | 4.5 |
| Min. High M.W. Aggregation | 2.4 | 1.9 | 1.7 | 3.1 |

Data from Table 17 indicates that the Minimum Tetramer Elaboration sample (dextrose and glycine) had a lower % tetramer elaboration than the Minimum High M.W. Aggregation sample

TABLE 17

% Tetramer Over Time: NF803

| Bag | T = 0 | T = 2 wks. | T = 4 wks. | T = 8 wks. |
|---|---|---|---|---|
| Minimum Tetramer Elaboration | 0.2 | 2.3 | 1.7 | 1.9 |
| Minimum High M.W. Aggregation | 0.2 | 2.4 | 1.8 | 2.4 |

Data from Table 18 suggests that the Minimum High M.W. Aggregation sample (glycine only) has a lower percentage of high M.W. polymer species after 8 weeks than the Minimum Tetramer Elaboration sample.

TABLE 18

Molecular Weight Distribution Over Time: NF803

| | | Area % Polymer Species | | | |
|---|---|---|---|---|---|
| Sample | Time (wks.) | 128K | 192K | 256K | 320 + K |
| Minimum Tetramer Elaboration | 2 | 17.5 | 18.0 | 15.8 | 46.3 |
| | 4 | 12.6 | 18.6 | 16.1 | 51.0 |
| | 8 | 12.8 | 17.9 | 15.3 | 52.0 |
| Minimum High M.W. Aggregation | 2 | 15.4 | 18.7 | 16.4 | 47.1 |
| | 4 | 12.8 | 18.8 | 16.4 | 50.2 |
| | 8 | 17.8 | 17.2 | 14.8 | 47.8 |

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams.

The claims should not be read as limited to the described order or elements unless stated to that effect. Therefore, all embodiments that come within the scope and spirit of the following claims and equivalents thereto are claimed as the invention.

What is claimed is:

1. A packaged hemoglobin solution comprising a polymerized hemoglobin solution having an oxyhemoglobin concentration of less than about 15% sealed within a flexible container comprising a polymer film having an oxygen permeability of about 0.05 to about 0.17 cc/m$^2$ per 24 hours per atmosphere at about 5° C. and an external relative humidity of about 60%.

2. The hemoglobin solution of claim 1 having a methemoglobin concentration of less than 8% for at least one year at about 5° C. and an external relative humidity of about 60%.

3. The hemoglobin solution of claim 1 wherein the solution comprises a cross-linked, polymerized, pyridoxylated hemoglobin.

4. The hemoglobin solution of claim 1 wherein the polymer film has a water vapor transmission rate of less than about 1.18 g/m$^2$ per 24 hours at about 5° C. and an external relative humidity of about 60%.

5. The hemoglobin solution of claim 1 further comprising ascorbic acid in a concentration of about 0.2 to about 1.0 g/L.

6. The hemoglobin solution of claim 1 further comprising glycine in a concentration of about 1.0 to 3.5 g/L.

7. The hemoglobin solution of claim 1 wherein said polymer film comprises an oxygen barrier layer.

8. The hemoglobin solution of claim 7 wherein said oxygen barrier layer comprises ethylene vinyl alcohol.

9. The hemoglobin solution of claim 1 wherein said polymer film comprises at least one polyolefin layer.

10. The hemoglobin solution of claim 9 wherein said at least one polyolefin layer comprises medium density polyethylene.

11. The hemoglobin solution of claim 9 wherein said at least one polyolefin layer and said oxygen barrier layer are co-extruded.

12. The hemoglobin solution of claim 9 wherein the polyolefin layer comprises linear low density polyethylene.

13. A packaged polymerized pyridoxylated hemoglobin solution comprising:
a polymerized, pyridoxylated hemoglobin solution having an oxyhemoglobin concentration of less than about 15% sealed within a flexible polymeric container comprising an oxygen barrier film having at least one layer, wherein said barrier film maintains the methemoglobin concentration of the solution below about 8.0% for at least one year at about 5° C.

14. The hemoglobin solution of claim 13 where the solution is a cross-linked, polymerized, pyridoxylated hemoglobin.

15. The hemoglobin solution of claim 13 further comprising an oxygen scavenger selected from the group consisting of ascorbic acid, and glycine.

16. The hemoglobin solution of claim 13 wherein the oxygen barrier layer comprises Polyvinylidene Chloride (PVDC).

17. A method of preparing a deoxygenated hemoglobin solution comprising sealing a polymerized hemoglobin solution within a flexible container comprising a polymer film having an oxygen permeability of about 0.05 to about 0.17 cc/m$^2$ per 24 hours per atmosphere at about 5° C. and an external relative humidity of about 60%, wherein the hemoglobin solution comprises at least one oxygen scavenger which reduces $O_2$.

18. The method of claim 17 wherein the oxygen scavenger is selected from the group consisting of ascorbic acid, dextrose and glycine.

19. The method of claim 18 wherein the oxygen scavenger is ascorbic acid in a concentration of about 0.2 to 1.0 g/L.

20. The method of claim 18 wherein the oxygen scavenger is glycine in a concentration of about 1.0 to 3.5 g/L.

21. A packaged hemoglobin solution with a methemoglobin concentration of less than about 8.0% for at least one year comprising a polymerized, pyridoxylated hemoglobin solution comprising an oxygen scavenger, wherein the solution has an oxyhemoglobin concentration of less than about 15% and is sealed within a flexible container comprising an oxygen barrier film having an oxygen permeability of about 0.05 to about 0.17 cc/m$^2$ per 24 hours per atmosphere at about 25° C. and an external relative humidity of about 60%.

22. The hemoglobin solution of claim 21 wherein the oxygen barrier film is a multilayer film comprising an oxygen barrier layer comprising ethylene vinyl alcohol or PVDC.

23. The hemoglobin solution of claim 22 wherein the oxygen barrier film further comprises an inert product contact layer which is a polyolefin.

24. The solution of claim 21 wherein the oxygen scavenger is selected from the group consisting of ascorbic acid, dextrose and glycine.

25. The solution of claim 24 wherein the oxygen scavenger is ascorbic acid in a concentration of about 0.2 to 1.0 g/L.

26. The solution of claim 24 wherein the oxygen scavenger is glycine acid in a concentration of about 1.0 to 3.5 g/L.

27. A packaged hemoglobin solution comprising: an oxygen-free, polymerized hemoglobin solution sealed with a flexible container comprising a polymer film having an oxygen permeability of about 0.05 to about 0.17 cc/m$^2$ per 24 hours per atmosphere at about 5° C. and an external relative humidity of about 60%.

* * * * *